United States Patent [19]

Regimand

[11] Patent Number: 4,874,950
[45] Date of Patent: Oct. 17, 1989

[54] ASPHALT CONTENT GAUGE WITH COMPENSATION FOR SAMPLE TEMPERATURE DEVIATIONS

[75] Inventor: Ali Regimand, Raleigh, N.C.

[73] Assignee: Troxler Electronic Laboratories, Inc., Research Triangle Park, N.C.

[21] Appl. No.: 175,144

[22] Filed: Mar. 30, 1988

[51] Int. Cl.$^4$ ............................................. G01N 23/05
[52] U.S. Cl. ........................... 250/390.04; 250/390.05
[58] Field of Search ........... 250/390 C, 390 R, 390 D, 250/390 E, 269, 265

[56] References Cited

U.S. PATENT DOCUMENTS

| | | | |
|---|---|---|---|
| 2,564,626 | 8/1951 | MacMahon et al. | 250/390.03 |
| 3,492,479 | 1/1970 | Lowery et al. | 250/390.04 |
| 3,761,712 | 9/1973 | Listerman | 250/390.05 |
| 4,164,655 | 8/1979 | Noma et al. | 250/390.04 |
| 4,362,939 | 12/1982 | Horiuchi et al. | 250/390.05 |
| 4,499,380 | 2/1985 | Aggour et al. | 250/390.05 |

OTHER PUBLICATIONS

Troxler Electronic Laboratories, Inc. Brochure on the Troxler 3241 Asphalt Content Gauge.

Primary Examiner—Janice A. Howell
Assistant Examiner—William F. Rauchholz
Attorney, Agent, or Firm—Bell, Seltzer, Park & Gibson

[57] ABSTRACT

The present invention relates to an improvement in a nuclear measuring gauge for measuring the composition of a hydrogen containing material by counting neutrons which are thermalized by the presence of the hydrogen in the material. The present invention is based upon the recognition that in measuring samples, such as hot asphalt, with such a gauge, the error which is introduced by temperature variations in a sample is a function of not only the temperature of the sample but also its hydrogen content. In accordance with the present invention, this inaccuracy is compensated for by applying to the measurement a correction factor which is a function of both the temperature of the sample and its hydrogen content.

7 Claims, 2 Drawing Sheets

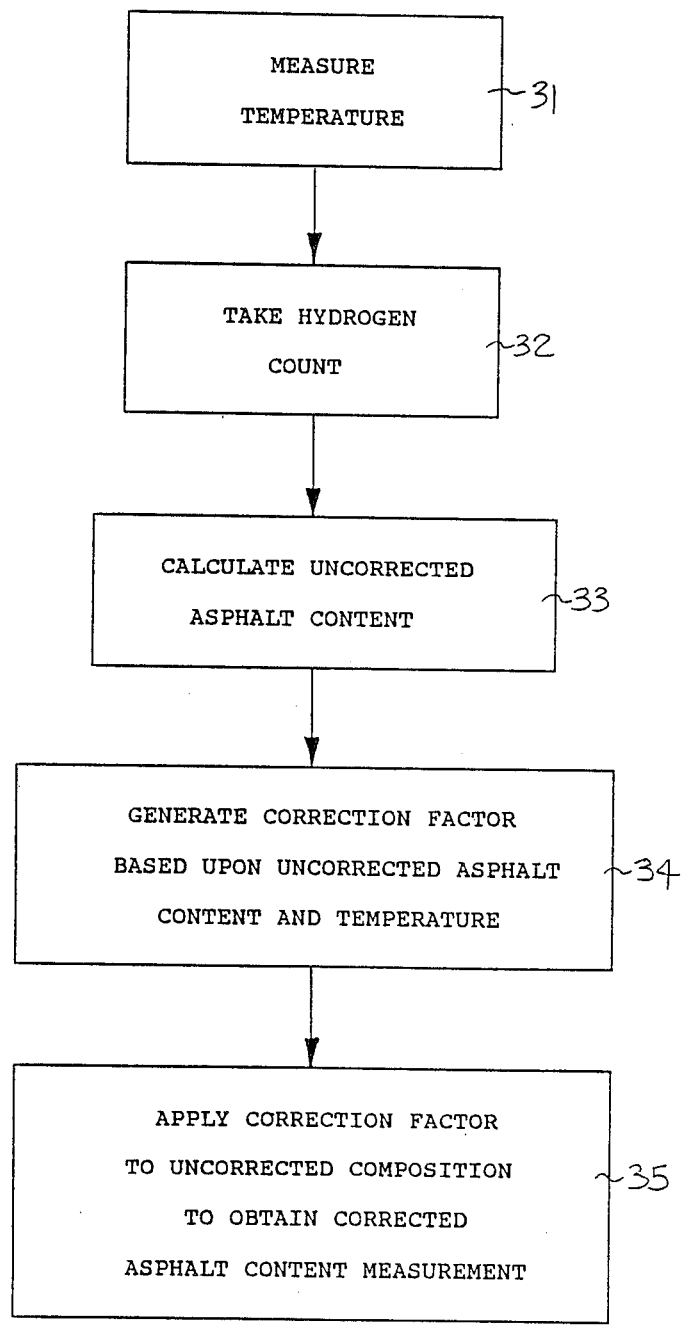

ASPHALT CONTENT GAUGE WITH COMPENSATION FOR SAMPLE TEMPERATURE DEVIATIONS

BACKGROUND OF THE INVENTION

Lowery, et al. U.S. Pat. No. 3,492,479 discloses a portable nuclear gauge which utilizes a fast neutron source and a thermal neutron detector for determining the composition of a bulk material, such as a bituminous paving mix, placed in a sample pan. This type of gauge relies upon the neutron moderating characteristics of hydrogen atoms present in the composition for determining, for example, the amount of asphalt in a paving mix or the amount of moisture in a building material. For these determinations it is known that the amount of asphalt and the amount of moisture can be related to the hydrogen content of the material, and the hydrogen content of the material can be determined by subjecting the sample to radiation from a fast neutron source and detecting neutrons which have been slowed or thermalized as a result of interaction with the hydrogen nuclei present in the sample. The number of thermalized neutrons detected over a period of time is counted, and this "count" is utilized in determining the asphalt content of the sample.

In operating the gauge, it is first necessary to establish a standard count for calibration purposes. This is accomplished using a standard sample which contains a layer of material known to produce some standard count, for example, a block of polyethylene. Then calibration curves are produced for the particular material being tested, by using carefully prepared samples of known asphalt content. After the calibration curves have been produced, unknown test samples can be placed in the gauge and counts are taken. By reference to the calibration curve, the corresponding asphalt content for that count can be read.

A more recent model of this gauge has been produced by applicant's assignee embodying the principles of the Lowery patent and sold as the "Model 3241 Asphalt Content Gauge" by Troxler Electronic Laboratories, Inc. This gauge includes a microprocessor to facilitate calibration and computation of the sample asphalt content. Calibration can be made by taking gauge counts on two samples of known asphalt content. The microprocessor then constructs a calibration equation from these data points, and the gauge provides a direct readout of the sample composition (percent asphalt), thus eliminating the necessity of calculations and reference to external calibration tables.

In using the gauge for measuring the asphalt content of hot asphalt samples, it was noted that the temperature of the sample has an effect upon the accuracy of the resulting reading and that variations in temperature from sample to sample can produce error or inaccuracy in the reading. In order to overcome this source of inaccuracy, the aforementioned Model 3241 gauge provided for the operator to manually enter into the instrument the temperature of the sample. Then a correction factor calculated as a function of the temperature was applied by the instrument to the experimental count in order to correct for the temperature effect. The accuracy and reliability of the Model 3241 gauge has been quite satisfactory and this gauge has gained a wide acceptance in the industry. However, applicants have now discovered how to further improve and enhance the accuracy level of the measurements made by the gauge.

SUMMARY OF THE INVENTION

The present invention is based upon the recognition and discovery that in measuring samples such as hot asphalt, the error introduced by temperature variations in a sample is a function not only of the temperature of the sample but also its asphalt content. Thus, at a relatively low asphalt content, one correction curve or correction factor would be utilized to correct for variations in temperature, while at a higher asphalt content a different correction curve or correction factor would be used. Moreover, it has been found that the percent correction as a function of temperature varies greatly as a function of the asphalt content.

Thus, it is an object of the present invention to provide a nuclear measuring gauge which more accurately compensates for deviations in the temperature of the sample by employing a correction factor which is a function of both the temperature of the sample and its asphalt content.

In accordance with the invention there is provided an improvement in the method of determining the hydrogen content of a hydrogen-containing material wherein a sample of the material is subjected to a neutron source and neutrons which are thermalized by the presence of the hydrogen in the material are detected to thus obtain a measurement of the hydrogen content of the material. The improvement comprises compensating for inaccuracy due to variations in the temperature of the sample by applying to the measurement a correction factor which is a function of both the temperature of the sample and the hydrogen content of the sample. More particularly, the step of compensating for inaccuracy by applying a correction factor comprises (a) measuring the temperature of the chamber containing the sample, (b) obtaining an uncorrected measurement of the hydrogen content of the sample, (c) generating a correction factor as a function of the temperature measured in step (a) and the uncorrected hydrogen measurement of step (b), and (d) applying the correction factor to the uncorrected hydrogen measurement to obtain a temperature compensated corrected measurement.

In accordance with a further aspect of the present invention there is provided an apparatus for measuring the hydrogen content of a material, wherein the apparatus comprises a measurement chamber for receiving a sample of the material, a source of fast neutrons mounted adjacent to the chamber, a detector for thermal neutrons mounted adjacent to the chamber, counting means cooperating with the thermal neutron detector for obtaining a count of the thermal neutrons, and means for compensating for deviations in the temperature of the sample as function of both the measured temperatures of the chamber containing the sample and the measured hydrogen content.

More specifically, the means for compensating for deviations in the temperature includes a temperature sensor means mounted adjacent to the chamber for measuring the temperature of the chamber containing the sample, means for storing a correction factor which varies as a function of both temperature and hydrogen content of the sample, means for calculating the correction factor based upon the measured temperature and upon the uncorrected measurement of sample hydrogen, and means for applying the correction factor to the uncorrected measurement of hydrogen content to thereby obtain a corrected measurement.

BRIEF DESCRIPTION OF THE DRAWINGS

Some of the features and advantages of the invention having been stated, others will become apparent from the detailed description which follows, and from the accompanying drawings, in which

FIG. 3 is a block diagram showing the operations performed by the gauge.

DETAILED DESCRIPTION OF THE DRAWINGS

Figure 1:
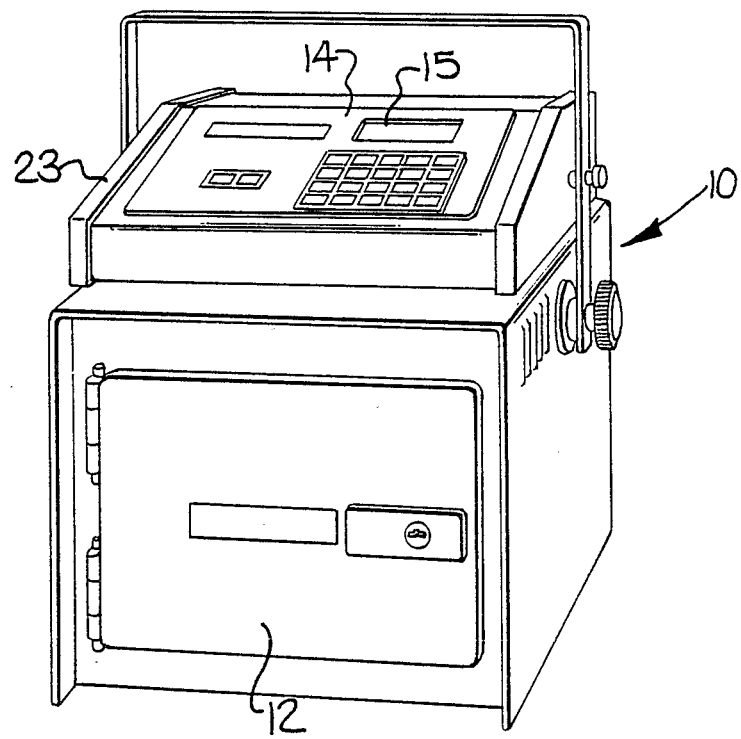
FIG. 1 is a perspective view showing an asphalt content gauge in accordance with the present invention.
Figure 2:
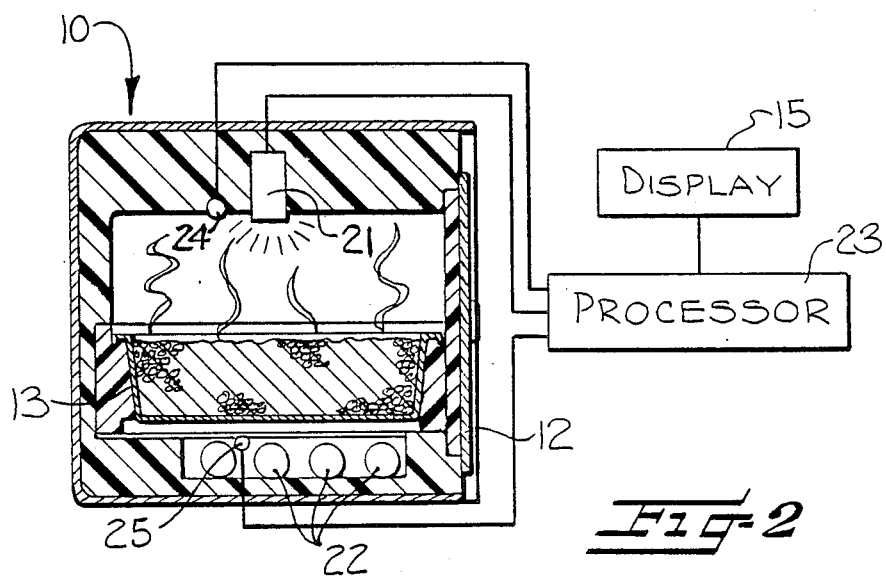
FIG. 2 is a schematic cross sectional view of the gauge.

Referring now more particularly to the drawings, the asphalt content gauge is indicated generally in FIG. 1 by the reference character 10 and comprises a generally rectangular housing 11 having a door 12 in the lower portion thereof providing access to a sample chamber. When the door 12 is opened, a removable sample pan 13 can be placed in the sample chamber as shown in FIG. 2. After the closing of the door, the gauge may be activated so as to measure the composition of the material in the sample pan. As illustrated, the upper portion of the gauge includes a control panel 14 including various controls for controlling the functions of the gauge and a display 15, which may be of any suitable known construction, such as a liquid crystal display device.

Referring now to FIG. 2, located in the interior upper portion of the gauge is a source 21 of fast neutrons. The source 21 may for example suitably comprise a Am-241:Be source. In the lower portion of the gauge beneath the sample pan are a series of detector tubes 22 for detecting thermal neutrons. While any suitable thermal neutron detector device can be employed, the illustrated embodiment employs $He^3$ detector tubes. The gauge also includes a data processor module 23 containing a microprocessor programed to perform various basic instrument functions including a measurement function, a calibration function and a test function. These same basic functions are carried out in commercially available asphalt content gauges, such as the Troxler 3241 gauge referred to earlier. Reference may be made to this gauge and its accompanying operation manual for a more complete description of the various functions and details of the operations which are carried out in these functions.

As shown in FIG. 2, the instrument is also provided with upper and lower temperature sensors 24, 25 located above and below the sample pan, respectively. The purpose of these temperature sensors is to determine the temperature of the sample so that an appropriate temperature correction can be made, as explained more fully hereinafter.

The gauge illustrated in FIGS. 1 and 2 is especially suited for rapidly measuring the asphalt content of bituminous paving mixes. Fast neutrons emitted by the Am-241:Be source are moderated by the hydrogen present in the asphalt sample. These slowed or thermalized neutrons are then detected by the thermal neutron detectors 22. The number of counts detected by the detectors is proportional to the asphalt content of the sample.

Since the gauge detects neutrons moderated by hydrogen in the total mix, i.e. the asphalt, the aggregate and moisture present in the aggregate, a careful calibration to isolate changes in asphalt content is important. Calibration will vary with the following factors:

(1) Different brands of asphalt will affect the calibration because of varying hydrogen concentration per weight of asphalt.

(2) Changing the aggregate mix, or source of supply, will change the amount of hydrogen present in the aggregate.

(3) Changes in the density and homogeneity of the mix will also affect calibration.

(4) The temperature of the sample and its effect on the ambient temperature inside the gauge will also affect the measurements. An increase in temperature increases the average speed of the neutrons and thus the average energy of the neutrons. This in turn will cause a decrease in the number of counts detected by the thermal neutron detectors 22.

Errors due to factors 1 and 2 above can be minimized by preparing calibration curves for each different brand of asphalt and type of aggregate mix. Errors due to variations in the density and homogeneity of the mix can be minimized by careful and consistent sample preparation.

Temperature correction is achieved in accordance with the present invention by means of the two temperature sensors 24, 25 inside the gauge. The two temperature readings from the sensors are averaged and are used in the temperature compensation of the asphalt measurement.

In accordance with the present invention it has been found that the effect of temperature on the asphalt content gauge varies with the amount of asphalt in the mix and appropriate compensation has to be made. This is achieved by preparing a calibration curve or calibration equation relating the error as a function of both temperature and asphalt content. Calibration curves or equations are obtained using samples of known asphalt content covering the entire usable range of asphalt content to be measured by the gauge. Then these correction factors are later used to correct the asphalt content measurement based both upon the initial asphalt content measurement and the temperature.

Thus the operations which are carried out by the processor unit 23 in obtaining an accurate measurement of asphalt content are represented in the block diagram of FIG. 3, and involve first measuring the temperature by use of the temperature sensors 24 and 25 (as indicated at 31), next taking a hydrogen count (32) over a predetermined period of time and calculating an uncorrected asphalt content based directly upon the hydrogen count (33). A correction factor is then generated based upon both the uncorrected asphalt content and the measured temperature as indicated at 34. A temperature compensated measurement is then obtained by applying the correction factor to the uncorrected asphalt content measurement as shown at 35.

The procedures of the present invention will be understood more fully from the following description of the calibration procedure and the temperature compensation procedure.

TEMPERATURE CALIBRATION PROCEDURE

The temperature compensation parameters are determined at the factory before the gauge is put into field use. The procedure is as follows:

1. Select samples of known asphalt content covering the usable range of the gauge (e.g. 2 percent to 10 percent asphalt content).

2. Measure these samples at room temperature and several different chamber temperatures. (Please note all temperature readings are averages of the two sensors.)

3. Find "percent difference" between counts at room temperature and all other temperatures.

4. Perform a straight line fit between temperature and "percent difference". So, $$\text{Percent difference} = A_1 + B_1 T \quad T = \text{temperature}$$
$$A_1, B_1 = \text{constants}$$

Repeat this for all the samples tested. Therefore at each percent asphalt there will be an equation such as the one above. Now a series of $A_1$'s and $B_1$'s are calculated for all the samples used.

5. Fit the $A_1$'s, and $B_1$'s against percent asphalt using a second order equation.

$$A_1 = a_1 + a_2 \% Ac + a_3 \% Ac^2$$
$$B_1 = b_1 + b_2 \% Ac + b_3 \% Ac^2$$
$$\% Ac = \% \text{Asphalt}$$
$\% Ac$ is known for each sample
$a_1, a_2, a_3 = \text{Constants}$
$b_1, b_2, b_3 = \text{Constants}$

GAUGE % ASPHALT CALIBRATION

The field calibration for % Asphalt Content (% AC) can be accomplished by the use of the linear equation $$\%AC = E + F \times \text{Count}$$

where E and F are calibration constants calculated by using at least two known % AC samples in the gauge. Each sample is measured and the counts are corrected for temperature effect by using the known % AC's along with the factory derived valued of $a_1$, $a_2$, $a_3$, $b_1$, $b_2$, and $b_3$ to calculate $A_1$ and $B_1$. With the known temperature value one can then calculate the percent difference in the counts. The counts are then corrected for temperature effect and the calibration constants E and F are calculated.

FIELD MEASUREMENTS WITH TEMPERATURE COMPENSATION

With the calibration constants thus known, temperature compensation can be readily applied. The following relationship is used for calculating the percent asphalt content:

$$\%AC = E + F \times (\text{Count}) \quad (1)$$

where E and F are the calibration constants derived above for the particular asphalt mix. The gauge measurement procedure involves the following steps:

(1) Take a hydrogen count. (Count)
(2) Take a temperature reading.
(3) Calculate %Ac from equation (1). This number is an estimated %Ac not corrected for temperature.
(4) Use %Ac to calculate $A_1$ and $B_1$ by $$A_1 = a_1 + a_2\%Ac + a_3\%Ac^2$$

$$B_1 = b_1 + b_2\%Ac + a_3\%Ac^2$$

(5) Use temperature reading to calculate percent difference. Percent Difference = $A_1 + B_1 T$
(6) Correct the measured count by percent difference. Adjusted Count = Count (1 + % difference)
(7) Finally, the temperature corrected %AC is corrected %AC = E + F × (Adjusted Count)

That which is claimed is:

1. An improvement in the method of determining the hydrogen content of a hydrogen-containing material wherein a sample of the material is subjected to a fast neutron source and neutrons which are thermalized by the presence of hydrogen in the material are detected to thus obtain a measurement of the hydrogen content of the material, said improvement comprising compensating for the inaccuracy due to variations in the temperature of the sample by applying to the measurement a correction factor which is a function of both the temperature of the sample and the hydrogen content of the sample.

2. The improvement according to claim 1 wherein said step of compensating for inaccuracy by applying a correction factor comprises
   (a) measuring the temperature adjacent the sample,
   (b) obtaining an uncorrected measurement of the hydrogen content of the sample,
   (c) generating a correction factor as a function of the temperature measured in step (a) and the uncorrected hydrogen content measurement of step (b), and
   (d) correcting the uncorrected measurement by applying the correction factor to the uncorrected hydrogen content measurement to obtain a temperature compensated corrected measurement.

3. The improvement according to claim 2 wherein said step (b) of obtaining an uncorrected measurement of the hydrogen content of the sample comprises obtaining an uncorrected count of thermalized neutrons from the sample, and said step (d) of correcting the uncorrected measurement comprises applying the correction factor to the uncorrected count of thermalized neutrons to obtain an adjusted count which compensates for the temperature of the sample.

4. A method of determining the asphalt content of a bituminous paving mix comprising
   placing a sample of the bituminous paving mix in a measurement chamber,
   subjecting the sample to a neutron source,
   detecting neutrons thermalized by the presence of hydrogen in the sample,
   counting the thermal neutrons detected during a predetermined period of time,
   calculating an uncorrected asphalt content from the thus obtained thermal neutron count by reference to the thermal neutron count and predetermined calibration data,
   measuring the temperature of the measurement chamber containing the sample,
   calculating a temperature correction factor which varies as a function of both temperature and asphalt content utilizing the measured temperature and the uncorrected measurement of asphalt content, and
   correcting the uncorrected asphalt content by applying the thus obtained correction factor to obtain a temperature compensated corrected asphalt content measurement.

5. A method as defined in claim 4 wherein (a) said step of calculating an uncorrected asphalt content is performed in accordance with the following relationship, Asphalt Content = E + F × (Count)

where E and F are calibration constants; and wherein (b) said step of calculating a temperature correction factor comprises calculating a correction factor which represents the percent difference in count rate due to temperature; and (c) said step of correcting the uncorrected asphalt content comprises adjusting the count rate based upon said correction factor to obtain an adjusted count, and calculating the corrected asphalt rate in accordance with the relationship, Corrected Asphalt Content = E + F × (Adjusted Count).

6. An apparatus for determining the composition of a hydrogen containing material said apparatus comprising a neutron source, detector means for detecting neutrons thermalized by a presence of hydrogen in the material, counting means cooperating with said detector means for obtaining the count of thermalized neutrons detected during a predetermined period of time, which count is proportional to the hydrogen content of the material, and means for compensating for inaccuracies due to variations in the temperature of the sample by applying to the measurement a correction factor which is a function of both the temperature of the sample and the uncorrected measurement of the hydrogen content of the sample.

7. An apparatus for determining the composition of hydrogen containing material comprising a measurement chamber for receiving a sample of the material, a neutron source mounted adjacent to the measurement chamber, detector means for detecting neutrons thermalized by the presence of hydrogen in the material, counter means for counting the thermalized neutrons detected during a predetermined period of time to thus obtain a measurement of the hydrogen content of the material, temperature sensor means mounted adjacent the measurement chamber for measuring the temperature of the measurement chamber containing the sample, means for calculating a correction factor which varies as a function of both the sample temperature and sample hydrogen content based upon the measured sample temperature and upon an uncorrected measurement of the sample hydrogen content, and means for applying the correction factor to the uncorrected measurement to obtain a temperature compensated corrected measurement of the sample hydrogen content.

* * * * *

UNITED STATES PATENT AND TRADEMARK OFFICE
CERTIFICATE OF CORRECTION

PATENT NO. : 4,874,950

DATED : October 17, 1989

INVENTOR(S) : Ali Regimand

It is certified that error appears in the above-identified patent and that said Letters Patent is hereby corrected as shown below:

Column 2, line 58 "temperatures" should be
  -- temperature --

Column 7, line 26, "a" should be -- the --

Signed and Sealed this

Twenty-fifth Day of September, 1990

Attest:

HARRY F. MANBECK, JR.

*Attesting Officer*  *Commissioner of Patents and Trademarks*